United States Patent
Sunami et al.

(10) Patent No.: US 9,563,968 B2
(45) Date of Patent: Feb. 7, 2017

(54) MEDICAL IMAGE PROCESSING APPARATUS

(71) Applicants: Toshiba Medical Systems Corporation, Otawara-shi (JP); Iwate Medical University, Morioka-shi (JP)

(72) Inventors: Kimiko Sunami, Otawara (JP); Kazumasa Arakita, Nasushiobara (JP); Masahiro Ozaki, Otawara (JP); Kunihiro Yoshioka, Morioka (JP); Ryoichi Tanaka, Morioka (JP); Kenta Muranaka, Morioka (JP)

(73) Assignees: Toshiba Medical Systems Corporation, Otawara-shi (JP); Iwate Medical University, Morioka-shi (JP)

( * ) Notice: Subject to any disclaimer, the term of this patent is extended or adjusted under 35 U.S.C. 154(b) by 0 days.

(21) Appl. No.: 14/723,908

(22) Filed: May 28, 2015

(65) Prior Publication Data

US 2015/0348261 A1 Dec. 3, 2015

(30) Foreign Application Priority Data

May 29, 2014 (JP) .................................. 2014-111737

(51) Int. Cl.
*G06K 9/00* (2006.01)
*G06T 7/20* (2006.01)
(Continued)

(52) U.S. Cl.
CPC ............. *G06T 7/2053* (2013.01); *A61B 6/032* (2013.01); *A61B 6/481* (2013.01); *A61B 6/5205* (2013.01);
(Continued)

(58) Field of Classification Search
None
See application file for complete search history.

(56) References Cited

U.S. PATENT DOCUMENTS

2010/0278425 A1* 11/2010 Takemoto ............. G06T 7/0079
382/173
2011/0319752 A1* 12/2011 Steinberg ................. A61B 6/12
600/424
(Continued)

FOREIGN PATENT DOCUMENTS

JP 2010/287948 * 7/2009
JP 2011-161104 8/2011
(Continued)

OTHER PUBLICATIONS

JP 2011-161104 machine translation Date Aug. 25, 2011.*

*Primary Examiner* — Nancy Bitar
(74) *Attorney, Agent, or Firm* — Oblon, McClelland, Maier & Neustadt, L.L.P.

(57) ABSTRACT

According to an embodiment, a medical image processing apparatus includes an extraction unit, a calculation unit, and a selection unit. The extraction unit extracts an image region having an image element value larger than a predetermined value from a first image of at least one time phase and second images of a plurality of time phases. The calculation unit calculates a feature quantity that fluctuates in accordance with motion of the image region for the first image of at least the one time phase and the second images of the time phases. The selection unit selects the first image and the second image having similar image features of the image region based on the feature quantity from among the first image of at least the one time phase and the second images of the time phases.

11 Claims, 7 Drawing Sheets (51) Int. Cl.
  *A61B 6/03*  (2006.01)
  *A61B 6/00*  (2006.01)
  *G06T 5/50*  (2006.01)

(52) U.S. Cl.
  CPC ....... G06T 5/50 (2013.01); *G06T 2207/10081* (2013.01); *G06T 2207/20224* (2013.01); *G06T 2207/30048* (2013.01)

(56) References Cited

U.S. PATENT DOCUMENTS

2013/0151163 A1\* 6/2013 Taylor ................ A61B 5/02007
  702/19
2015/0161790 A1\* 6/2015 Takahashi ............ A61B 5/0245
  600/424

FOREIGN PATENT DOCUMENTS

| JP | 2012-200285 | 10/2012 |
| JP | 2013-525056 | 6/2013 |

\* cited by examiner

FIG. 9

MEDICAL IMAGE PROCESSING APPARATUS

CROSS-REFERENCE TO RELATED APPLICATIONS

This application is based upon and claims the benefit of priority from the prior Japanese Patent Application No. 2014-111737, filed May 29, 2014 the entire contents of which are incorporated herein by reference.

FIELD

Embodiments described herein relate generally to a medical image processing apparatus.

BACKGROUND

X-ray computed tomography apparatuses are frequently used for evaluation of the coronary lumen of the heart. A method of removing a calcification region and a stent region by subtracting a non-contrast CT image from a contrast CT image to reduce the influence of the calcification region and stent on the evaluation of lumen is known. In subtraction processing for a heart region, motions of the calcification region and the stent region accompanying pulsation of the heart exert an enormous influence on the image quality of subtraction images. Further, the combination of volume images intended for subtraction processing has an enormous influence on the image quality of subtraction images. If, for example, geometrical features such as the position, shape, or CT value of the calcification region and stent region are different between a non-contrast CT image and a contrast CT image, the image quality of a subtraction image is degraded. An observer judges the combination of a non-contrast CT image and a contrast CT image by visual inspection. Thus, the work flow related to subtraction processing is prolonged. In addition, empirical knowledge is needed for the selection of the optimum combination by visual inspection and thus, the combination and subtraction images vary among individuals.

DETAILED DESCRIPTION

In general, according to one embodiment, a medical image processing apparatus includes an extraction unit, a calculation unit, and a selection unit. The extraction unit extracts an image region having an image element value larger than a predetermined image element value from a first image of at least one time phase collected in first imaging and second images of a plurality of time phases collected in second imaging. The calculation unit calculates a feature quantity that fluctuates in accordance with motion of the image region for the first image of at least the one time phase and the second images of the time phases. The selection unit selects the first image and the second image having similar image features of the image region based on the feature quantity from among the first image of at least the one time phase and the second images of the time phases.

Hereinafter, a medical image processing apparatus according to the present embodiment will be described with reference to the drawings.

The medical image processing apparatus according to the present embodiment is a computer apparatus that processes medical images generated by a medical modality. The medical image processing apparatus according to the present embodiment processes medical images generated by any medical modality such as an X-ray computed tomography apparatus, a magnetic resonance imaging apparatus, an ultrasonic diagnosis apparatus, and a nuclear medical diagnosis apparatus. Hereinafter, if not specifically mentioned, the medical image processing apparatus according to the present embodiment is assumed to process CT images generated by an X-ray computed tomography apparatus.

The medical image processing apparatus according to the present embodiment is a computer apparatus that performs image processing of CT images collected by an X-ray computed tomography apparatus. The X-ray computed tomography apparatus images an imaging region of a subject using X-rays. More specifically, the X-ray computed tomography apparatus generates X-rays from an X-ray tube while rotating a rotation frame on which the X-ray tube and an X-ray detector are mounted and detects X-rays generated by the X-ray tube and having passed through a subject by the X-ray detector. The X-ray computed tomography apparatus acquires raw data in accordance with X-rays detected by the X-ray detector through a data collection circuit (DAS: Data Acquisition System) and reconstructs CT image data by an image reconstruction circuitry based on the collected raw data. Incidentally, the medical image processing apparatus according to the present embodiment may be incorporated into the X-ray computed tomography apparatus or a computer apparatus separate from the X-ray computed tomography apparatus. To provide a concrete description below, the medical image processing apparatus is assumed to be a computer apparatus separate from the X-ray computed tomography apparatus.

It is also assumed that a subject according to the present embodiment contains an X-ray high-absorbance material. Concrete examples of the X-ray high-absorbance material according to the present embodiment include a calcification portion and a stent. The calcification portion is a calcium component deposited on the blood vessel wall or the like of the subject. The stent is an instrument to hold the lumen of the blood vessel. The stent is used, for example, for treatment of calcification. Any part such as the heart, the head, and the abdomen including the blood vessel may be selected as the imaging region of the subject according to the present embodiment. In the description that follows, however, the imaging region according to the present embodiment is assumed to be the heart as an object of the evaluation of coronary lumen for which subtraction processing is clinically used frequently.

Figure 1:
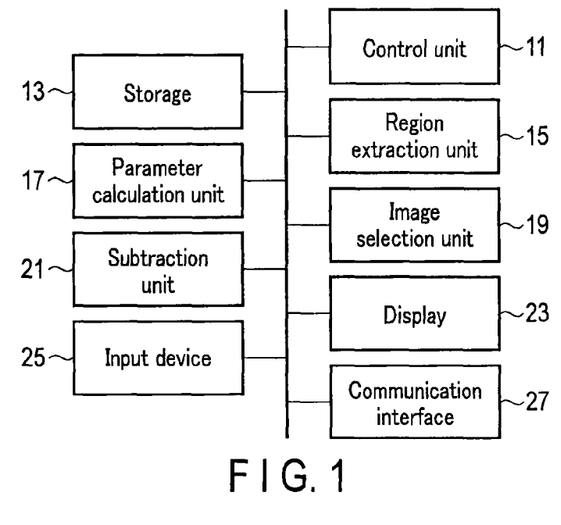
FIG. 1 is a diagram showing the configuration a medical image processing apparatus according to the present embodiment.

FIG. 1 is a diagram showing the configuration a medical image processing apparatus according to the present embodiment. As shown in FIG. 1, the medical image processing apparatus according to the present embodiment includes a control unit 11 as a center, a storage 13, a region extraction unit 15, a parameter calculation unit 17, an image selection unit 19, a subtraction unit 21, a display 23, an input device 25, and a communication interface 27.

The storage 13 is a storage unit that stores various kinds of information such as a hard disk drive (HDD) and a solid state drive (SSD). More specifically, the storage 13 is a storage unit that stores data of a plurality of CT image groups. For example, the storage 13 stores data of a first CT image group collected by an X-ray computed tomography apparatus in first imaging and data of a second CT image group collected by the X-ray computed tomography apparatus in second imaging. The first imaging is assumed to be temporarily performed before the second imaging. Each CT image group may be configured is a single CT image or a plurality of CT images. A CT image is an image that shows a spatial distribution of CT values collected by an X-ray computed tomography apparatus. Each CT image contained in a CT image group is associated with the time phase such as a heart phase or a breathing phase. The first CT image group and the second CT image group may be a contrast CT image group and a non-contrast CT image group or both of the first CT image group and the second CT image group may be contrast CT image groups. A non-contrast CT image group contains a plurality of CT images in time series concerning a plurality of time phases intended for a subject in which the imaging part is not visualized. A contrast CT image group contains a plurality of CT images in time series concerning a plurality of time phases intended for a subject in which the imaging part is visualized by a contrast agent. Time phases associated with a CT image include a heart phase and a breathing phase. Non-contrast CT image group data and contrast CT image group data are stored in the storage 13.

The region extraction unit 15 extracts a specific image region having a CT value larger than a predetermined CT value from a first CT image of each time phase contained in the first CT image group and a second CT image of each time phase contained in the second CT image group. More specifically, as a specific image region, an image region concerning an X-ray high-absorbance material (hereinafter, called an X-ray high-absorbance region) is extracted by image processing. Each image element constituting an X-ray high-absorbance region has a CT value larger than a predetermined CT value capable of recognizing the X-ray high-absorbance region from image regions of other tissues or materials. Incidentally, an image region is assumed to be a set of a plurality of image elements.

The parameter calculation unit 17 calculates feature quantities that fluctuate in accordance with motion of an X-ray high-absorbance region for a first CT image of each time phase contained in the first CT image group and a second CT image of each time phase contained in the second CT image group. The feature quantities determine image features of an X-ray high-absorbance region. Image features contain at least one of geometrical features and image element value features. Geometrical features of an X-ray high-absorbance region include, for example, the position, shape, or size of the X-ray high-absorbance region. Image element value features of an X-ray high-absorbance region include, for example, CT values of the X-ray high-absorbance region and statistics of CT values. A feature quantity is calculated based on at least one of the CT value and the number of image elements of an X-ray high-absorbance region. Feature quantities include, for example, the movement amount, the average CT value, the total CT value, and the volume of an X-ray high-absorbance region.

The image selection unit 19 selects a first CT image and a second CT image having similar image features of the X-ray high-absorbance region from first CT images of a plurality of time phases contained in the first CT image group and second CT images of a plurality of time phases contained in the second CT image group based on feature quantities calculated by the parameter calculation unit 17. The image selection unit 19 may select a first CT image and a second CT image concerning the same time phase if image features of the X-ray high-absorbance region are similar or a first CT image and a second CT image concerning different time phases.

The subtraction unit 21 performs subtraction processing on a CT image. More specifically, the subtraction unit 21 generates a subtraction image based on the first CT image and the second CT image selected by the image selection unit 19.

Incidentally, the region extraction unit 15, the parameter calculation unit 17, the image selection unit 19, and the subtraction unit 21 may be implemented by a single image processing circuitry or individual image processing circuitry. An image processing circuitry includes a processing circuitry such as CPU, MPU, and GPU and a storage unit such as HDD, SSD, ROM, and RAM.

The display 23 displays various kinds of information such as a CT image and a subtraction image. As a display, for example, a CRT display, a liquid crystal display, an organic EL display, or a plasma display can appropriately be used.

The input device 25 accepts various commands information input from the user through an input device. As an input device, a keyboard, a mouse, and various switches can be used.

The communication interface 27 is a network interface to communicate with other computer apparatuses connected to a network. For example, the communication interface 27 receives data of CT images from a picture archiving and communication system (PACS) via a network or transmits subtraction image data. The communication interface 27 may also receive CT image data from an X-ray computed tomography apparatus via a network.

The control unit 11 functions as a center of a medical image processing apparatus according to the present embodiment. The control unit 11 includes a processing circuitry such as CPU and MPU and a storage unit such as ROM and RAM. The control unit 11 loads an image processing program according to the present embodiment from the storage 13 or the like and controls various structural elements according to the image processing program. Accordingly, the selection of the optimum combination of time phases and subtraction processing according to the present embodiment are performed.

Hereinafter, an operation example of a medical image processing apparatus according to the present embodiment will be described. In the description that follows, it is assumed that data of the first CT image group is data of a non-contrast CT image group and data of the second CT image group is data of a contrast CT image group. A CT image according to the present embodiment may be a slice image showing the two-dimensional spatial distribution of CT values or a volume image showing the three-dimensional spatial distribution thereof. A slice is configured by a plurality of pixels arranged two-dimensionally and a volume image is configured by a plurality of voxels arranged three-dimensionally. A CT value is allocated to a pixel or a voxel. Hereinafter, it is assumed that the CT image is a volume image to concretely describe an operation example according to the present embodiment. It is also assumed that each non-contrast volume image contained in a non-contrast volume image group and each contrast volume image contained in a contrast volume image group are associated with a heart phase.

Figure 2:
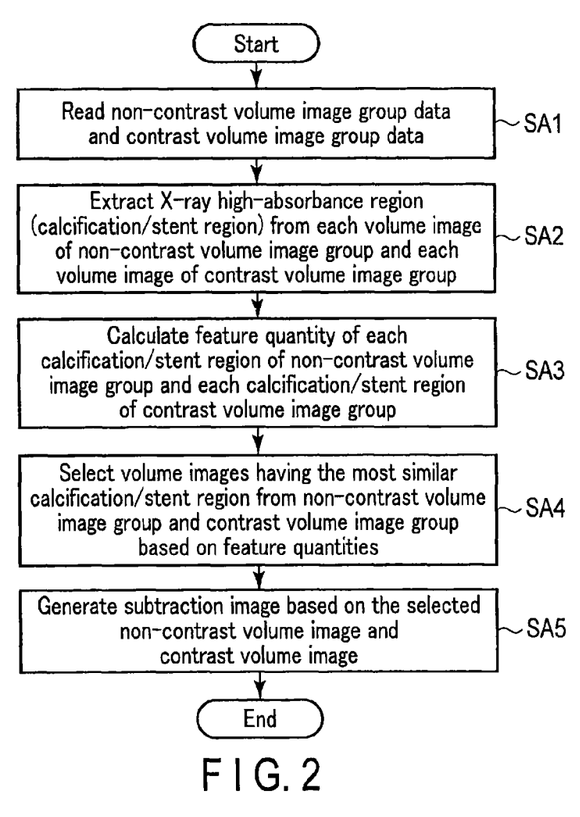
FIG. 2 is a diagram showing a set of processing related to the identification of the optimum combination of time phases and subtraction processing performed under the control of a control unit according to the present embodiment.

FIG. 2 is a diagram showing a set of processing related to the selection of the optimum combination of time phases and subtraction processing performed under the control of the control unit 11 according to the present embodiment.

When a start instruction of the processing is issued via the input device 25, the control unit 11 reads data of a non-contrast CT image group and data of a contrast CT image group provided by subtraction processing from the storage 13 (step SA1). Data of the non-contrast volume image group and data of the contrast volume image group are volume image groups having the same subject serving as a subject. A non-contrast volume image contained in the non-contrast volume image group contains an X-ray high-absorbance region concerning an X-ray high-absorbance material. A contrast volume image contained in the contrast volume image group contains, in addition to an X-ray high-absorbance region, an image region concerning a contrast blood vessel (hereinafter, called a contrast blood vessel region). There is no need for the control unit 11 to read data of all volume images of the non-contrast volume image group and the contrast volume image group. For example, the control unit 11 may read, among all volume images contained in the non-contrast volume image group and the contrast volume image group, only data of volume images in a predetermined heart phase range. As the heart phase range, a range in which motion of the X-ray high-absorbance material due to pulsation of the heart is relatively small, for example, 10 phases of 70% to 79% are suitable. The range of the heart phase to be read can be set to any range via the input device 25 or the like.

When step SA1 is performed, the control unit 11 causes the region extraction unit 15 to perform extraction processing (step SA2). In step SA2, the region extraction unit 15 extracts an X-ray high-absorbance region from a non-contrast volume image of each heart phase of the non-contrast volume image group and a contrast volume image of each heart phase of the contrast volume image group read by the control unit 11.

Figure 3A:
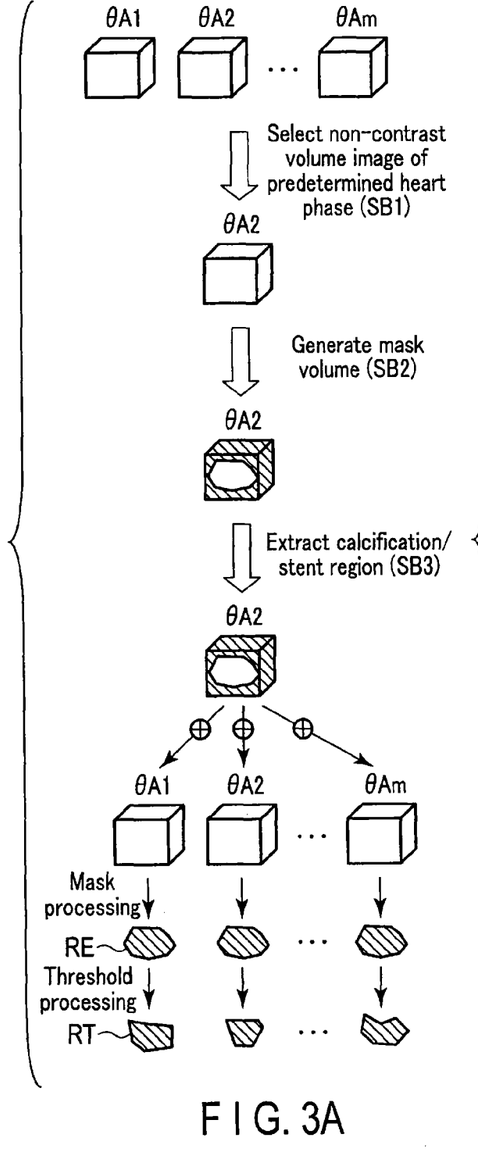
FIG. 3A is a diagram schematically showing the flow of extraction processing for a non-contrast volume image group by a region extraction unit performed in step SA2.
Figure 3B:
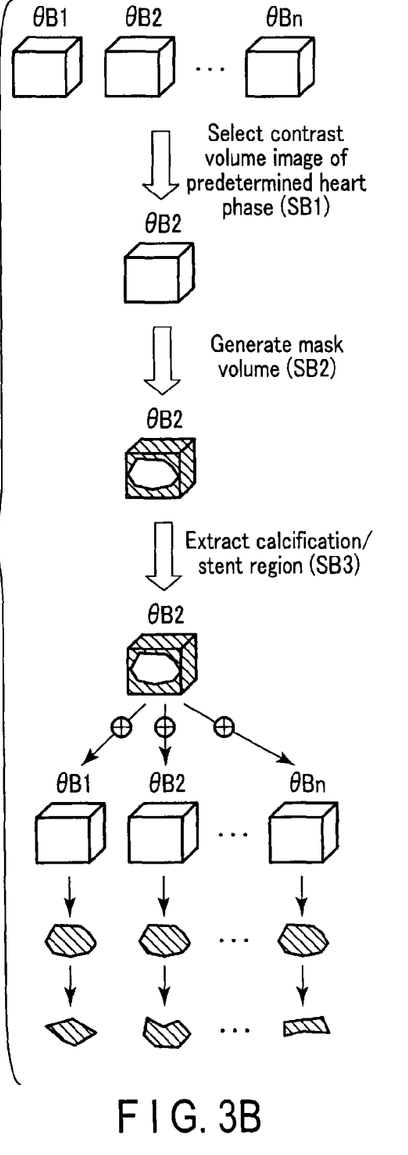
FIG. 3B is a diagram schematically showing the flow of extraction processing for a contrast volume image group by a region extraction unit performed in step SA2.

FIG. 3 is a diagram schematically showing the flow of extraction processing by the region extraction unit 15 performed in step SA2. FIG. 3A is a diagram schematically showing the flow of extraction processing for the non-contrast volume image group. FIG. 3B is a diagram schematically showing the flow of extraction processing for the contrast volume image group. The extraction processing is performed separately for the non-contrast volume image group and the contrast volume image group read in step SA1. It is assumed here that the non-contrast volume image group read in step SA1 has m numbers of non-contrast volume images from which of the heart phase θA1 to θAm and the contrast volume image group has n numbers of non-contrast volume images from which of the heart phase θB1 to θBn. m and n may be equal or different. From the point of the optimum combination of time phases, one of m and n may be 1, but the other needs to be equal to 3 or greater. In the description that follows, m and n are each assumed to be equal to 3 or greater.

As shown in FIG. 3A and FIG. 3B, the region extraction unit 15 first extracts a volume image of a predetermined heart phase used for a mask volume image from each of the non-contrast volume image group and the contrast volume image group (step SB1). As the predetermined heart phase, a time phase in which motion of the heart due to pulsation is relatively small is set. More specifically, as the predetermined heart phase, mesodiastolic, that is, the heart phase of 75% may be set. Alternatively, as the predetermined heart phase, an intermediate phase, the initial phase, or the final phase of the heart phase range read in step SA1. Incidentally, the predetermined heart phase can be set to any value by the user via the input device 25 or the like. For example, as shown in FIG. 3A and FIG. 3B, the region extraction unit 15 selects the non-contrast volume image of the heart phase θA2 from the non-contrast volume image group and the contrast volume image of the heart phase θB2 from the contrast volume image group.

When step SB1 is performed, the region extraction unit 15 generates a mask volume image in which the image region other than the X-ray high-absorbance region is a mask region based on the volume images selected in step SB1 (step SB2). The generation processing of a mask volume image is performed separately for the non-contrast volume image and the contrast volume image selected in step SB1.

Figure 4:
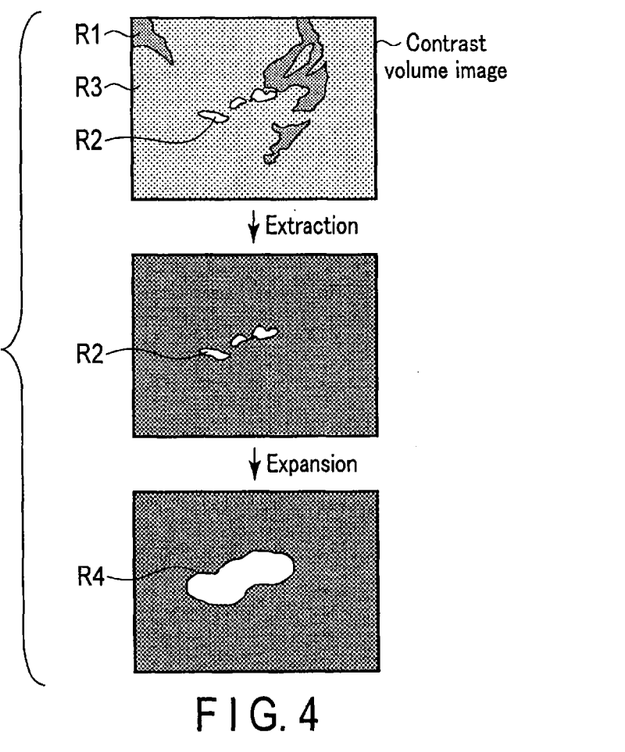
FIG. 4 is a diagram stepwise showing processing content of generation processing of a mask volume image performed by the region extraction unit in step SA2 of FIG. 3A and FIG. 3B.

FIG. 4 is a diagram stepwise showing processing content of the generation processing of a mask volume image by the region extraction unit 15. In FIG. 4, only contrast volume images are illustrated, but a mask volume image is also generated for the non-contrast volume image by a similar method.

As shown in FIG. 4, the contrast volume image (likewise for the non-contrast volume image) selected in step SB1 contains, in addition to an image region (hereinafter, called a human body tissue region) R1 corresponding to human body tissues (more specifically, soft tissues, water, and fat tissues) such as the cardiac muscle, an X-ray high-absorbance region R2 corresponding to an X-ray high-absorbance material. As the X-ray high-absorbance region, an image region corresponding to a calcification portion (hereinafter, called a calcification region) and an image region corresponding to a stent (hereinafter, called a stent region) can be cited. The contrast volume image also contains an image region (hereinafter, called a contrast agent region) R3 corresponding to a contrast agent injected into the blood vessel. In general, the CT value of the contrast agent region R3 is greater than the CT value of the human body tissue region R1 and smaller than the CT value of the X-ray high-absorbance region R2. For example, the CT value of the X-ray high-absorbance region R2 is distributed in the range of 600 to 2,000 H.U., the CT value of the contrast agent region R3 is distributed in the range of 300 to 400 H.U., and the CT value of the human body tissue region R1 is distributed in the range of −100 to +100 H.U. Incidentally, each volume image does not necessarily need to contain both of a calcification region and a stent region and needs to contain only one of a calcification region and a stent region. In addition, there is no difference between processing when both of a calcification region and a stent region are contained in each volume image and processing when both are not contained. Thus, to simplify the description that follows, it is assumed that each volume image contains both of a calcification region and a stent region.

First, the region extraction unit 15 performs threshold processing on a volume image to extract a calcification region and a stent region from the volume image. The threshold concerning threshold processing on a non-contrast volume image is set to a CT value capable of recognizing a calcification region and a stent region from a human body tissue region. The region extraction unit extracts a calcification region and a stent region by performing threshold processing having the relevant CT value on a non-contrast volume image. Incidentally, a calcification region and a stent region are not extracted by being distinguished. Here, a calcification region and a stent region will together be called a calcification/stent region R2. That is, a calcification/stent region is extracted from the non-contrast volume image.

The threshold concerning threshold processing on a contrast volume image is set to a CT value capable of recognizing the calcification/stent region R2 from the contrast agent region R3. The region extraction unit 15 extracts the calcification/stent region R2 by performing threshold processing having the relevant CT value on a contrast volume image. Incidentally, the contrast agent region R3 and the calcification/stent region R2 contained in a contrast volume image may have a mutually overlapping CT value range. In such a case, the region extraction unit 15 extracts a combined region of the contrast agent region R3 and the calcification/stent region R2 from a contrast volume image by threshold processing and distinguishes the contrast agent region R3 and the calcification/stent region R2 contained in the combined region based on the Bayes estimation to remove the contrast agent region R3 from the combined region. Accordingly, the calcification/stent region R2 is extracted from the contrast volume image.

Next, the region extraction unit 15 expands the extracted calcification/stent region R2 by a predetermined number of voxels three-dimensionally from the surface. The predetermined number of voxels is set to a number that falls within a calcification/stent region R4 after the expansion even if the position or shape of the calcification/stent region R2 in a volume image changes accompanying the pulsation of the heart. For example, the predetermined number of voxels may be set to, for example, ten voxels.

Then, the region extraction unit 15 allocates a 0 value to voxels constituting the calcification/stent region R4 after the expansion and allocates a predetermined value (for example, a 1 value or 255 value) to voxels constituting an image region other than the calcification/stent region R4 after the expansion to generate a mask volume image. The image region other than the calcification/stent region R4 after the expansion is set as a mask region and the calcification/stent region R4 after the expansion is set as a non-mask region.

In this manner, the region extraction unit 15 generates, based on a non-contrast volume image, a mask volume image (hereinafter, called a non-contrast mask volume image) in which the image region other than the calcification/stent region is set as a mask region and, based on a contrast volume image, a mask volume image (hereinafter, called a contrast mask volume image) in which the image region other than the calcification/stent region is set as a mask region.

When step SB2 is performed, the region extraction unit 15 extracts a calcification/stent region from a volume image concerning each heart phase contained in each volume image group using the mask volume image generated in step SB2 (step SB3). More specifically, the region extraction unit 15 extracts an image region (hereinafter, called an extraction region) RE matching a non-mask region from a non-contrast volume image concerning each of the heart phases θA1 to θAm of a non-contrast volume image group using a non-contrast mask volume image. The extraction region RE contains an image region such as a human body tissue region other than a calcification/stent region. The region extraction unit 15 extracts a calcification/stent region RT from the extraction region RE by threshold processing in which the CT value (for example, 600 HU to 2000 HU) exhibited by a standard X-ray high-absorbance region is used as a reference. That is, a set of image elements having a CT value larger than the relevant threshold of the extraction region RE is extracted as the calcification/stent region RT. In this manner, the calcification/stent region RT concerning each of the heart phases θA1 to θAm is extracted from a non-contrast volume image concerning each of the heart phases θA1 to θAm of a non-contrast volume image group. Similarly, the region extraction unit 15 extracts the calcification/stent region RT concerning each of the heart phases θB1 to θBn from a contrast volume image concerning each of the heart phases θB1 to θBn of a contrast volume image group.

With the above processing, the extraction processing by the region extraction unit 15 in step SA2 is completed.

When step SA2 is performed, the control unit 11 causes the parameter calculation unit 17 to perform calculation processing (step SA3). In step SA3, the parameter calculation unit 17 calculates feature quantities that fluctuate in accordance with motion of calcification/stent regions concerning each of the heart phases θA1 to θAm of a non-contrast volume image group and concerning each of the heart phases θB1 to θBn of a contrast volume image group. As described above, for example, the movement amount, the average CT value, the total CT value, and the volume of calcification/stent regions are calculated as feature quantities.

As the total CT value, the total value of CT values of all voxels constituting a calcification/stent region concerning phases to be calculated. The CT value is underestimated accompanying motion of a calcification portion or a stent. Hereinafter, the underestimation of the CT value will briefly be described. To simplify the description, the original CT value of the calcification region is assumed to be 600 H.U. If a calcification portion is completely stopped, all voxels constituting the calcification region corresponding to the calcification portion have the CT value of 600 H.U. However, if a calcification portion moves violently, the CT value on an end of the calcification region corresponding to the calcification portion is spread to image regions showing surrounding human body tissues or a contrast agent (Blurring) due to insufficient time resolution. Thus, the CT value on an end of the calcification region is lower than 600 H.U., which should be held by the calcification region. In this case, the CT value of the calcification/stent region decreases with more violent motion of the calcification portion. The total CT value changes also in accordance with changes of the shape of a calcification region or a stent region accompanying the pulsation.

As the average CT value, a value is calculated by dividing the total CT value of a calcification/stent region concerning the phase to be calculated by the number of a plurality of voxels constituting the calcification/stent region. The average CT value is underestimated accompanying motion of a calcification portion or a stent. Thus, the average CT value of the calcification/stent region decreases with more violent motion of calcification portion.

As the movement amount of a calcification/stent region, the movement amount of the calcification/stent region concerning the phase to be calculated with respect to the calcification/stent region concerning the previous phase of the phase to be calculated. The movement amount is defined by a difference between the total CT value of a calcification/stent region of the phase to be calculated and the total. CT value of the calcification/stent region of the previous phase of the phase to be calculated. The total CT value is defined as the total value of CT values of a plurality of voxels constituting a calcification/stent region. The previous phase may be the heart phase one phase prior to the phase to be calculated or the heart phase a predetermined phase prior to the phase to be calculated. Similarly, the movement amount of the calcification/stent region concerning the phase to be calculated with respect to the calcification/stent region concerning the subsequent phase of the phase to be calculated is calculated. The subsequent phase may be the heart phase one phase subsequent to the phase to be calculated or the heart phase a predetermined phase subsequent to the phase to be calculated. The movement amount largely depends mainly on change over time of the position or shape of the calcification/stent region. If the movement amount has a 0 value, this shows that there is no change of the position or shape of the calcification/stent region.

As the volume, the number of all voxels constituting a calcification/stent region concerning the phase to be calculated is counted. The volume changes in accordance with change in shape of a calcification region or a stent region accompanying the pulsation. In addition, the calcification/stent region may shrink due to underestimation of the CT value accompanying motion of a calcification portion or a stent. That is, the calcification/stent region in step SA3 is generated by the threshold processing in which the CT value is used as a reference in step SB3. If, as described above, a calcification portion or a stent moves, the CT value decreases and a voxel that should be extracted as a calcification/stent region may not be extracted. Thus, the volume of a calcification/stent region may also change due to underestimation of the CT value accompanying the pulsation.

Figure 5:
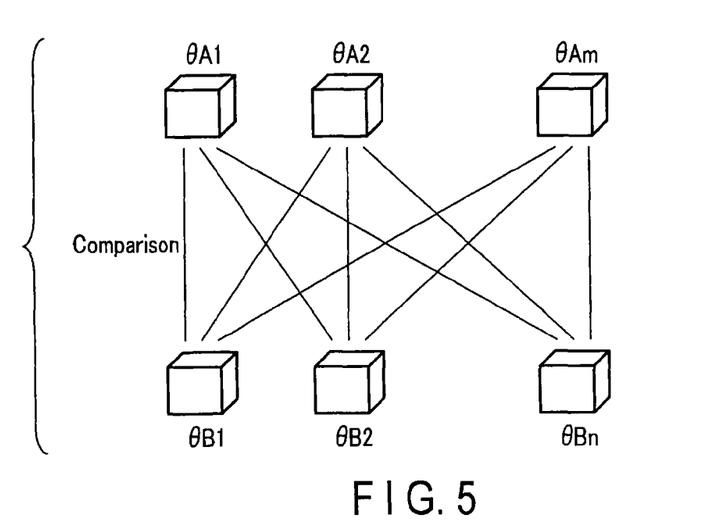
FIG. 5 is a diagram showing combinations of comparison of feature quantities performed by an image selection unit in step SA4 of FIG. 3A and FIG. 3B.

When step SA3 is performed, the control unit 11 causes the image selection unit 19 to perform selection processing (step SA4). In step SA4, the image selection unit 19 selects a non-contrast CT volume image and a contrast CT volume image having the most similar calcification/stent region from among volume images of the heart phases θA1 to θAm of a non-contrast volume image group and images of the heart phases θB1 to θBn of a contrast volume image group based on feature quantities calculated in step SA3. More specifically, as shown in FIG. 5, the image selection unit 19 first compares each of a plurality of non-contrast volume images contained in the non-contrast volume image group with a plurality of contrast volume images contained in the contrast volume image group in terms of each feature quantity calculated in step SA3. In other words, each feature quantity calculated in step SA3 is compared in all combinations of one heart phase of the heart phases θA1 to θAm of the non-contrast volume image group and one heart phase of the heart phases θB1 to θBn of the contrast volume image group. Based on the comparison, the image selection unit 19 calculates for each feature quantity a score showing the degree of similarity of image features of the calcification/stent region based on the feature quantity. As the score, the product of feature quantities of the same type of the calcification/stent region of a non-contrast volume image and the calcification/stent region of a contrast volume image can typically be cited. However, the score is not limited to the product only and may be the sum of feature quantities of the same type.

Figure 6:
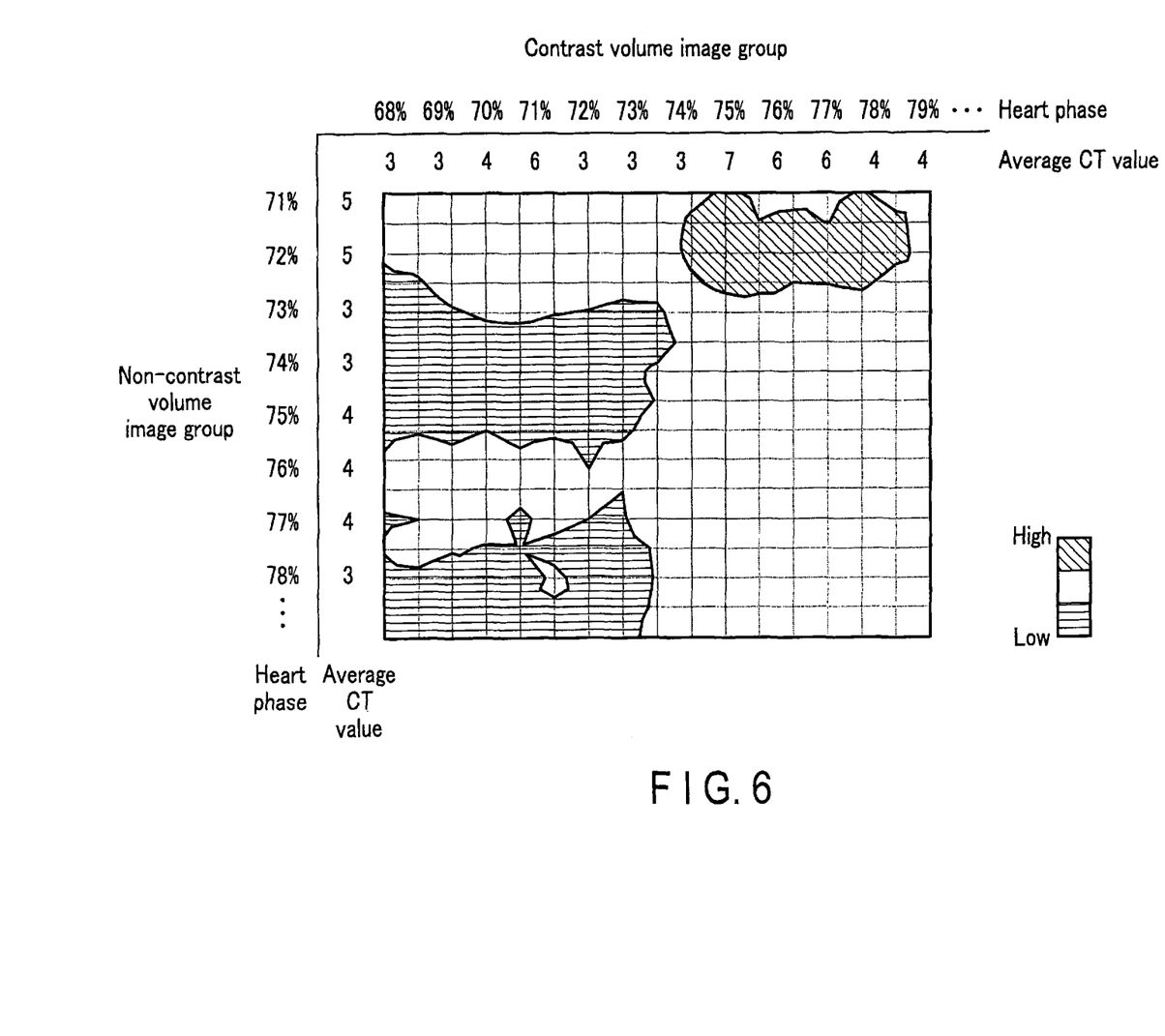
FIG. 6 is a diagram showing a comparison example of average CT values of a non-contrast volume image group and a contrast volume image group performed by the image selection unit in step SA4 of FIG. 3A and FIG. 3B.

FIG. 6 is a diagram showing a comparison example of average CT values of a non-contrast volume image group and a contrast volume image group. The vertical an Xis in FIG. 6 shows the heart phase of a non-contrast volume image group and the horizontal an Xis shows the heart phase of a contrast volume image group. The number corresponding to each heart phase shows the average CT value of the calcification/stent region concerning the heart phase. For example, the average CT value of the calcification/stent region of the heart phase 71% of the non-contrast volume image group is "5" and the average CT value of the calcification/stent region of the heart phase 71% of the non-contrast volume image group is "6". The intersection of each heart phase of the non-contrast volume image group and each heart phase of the contrast volume image group shows the score based on the average CT value (hereinafter, called the average CT value score). In FIG. 6, the value of the average CT value score is shown by a hatching pattern. In FIG. 6, the average CT value score is stepwise by three types of hatching. For example, a region indicated by right down oblique lines shows a high-level average CT value, a region indicated by a blank shows a medium average CT value, and a region indicated by horizontal lines shows a low-level average CT value. For example, the average CT value score of a combination of the heart phase 71% of the non-contrast volume image group and the heart phase 71% of the contrast volume image group is "5"×"6"="30". Using the above method, average CT value scores of all combinations of each non-contrast volume image of the non-contrast volume image group and each contrast volume image of the contrast volume image group are calculated.

For the movement amount, the total CT value, and the volume of a calcification/stent region, like the average CT value, the image selection unit 19 calculates scores of all combinations of each non-contrast volume image of the non-contrast volume image group and each contrast volume image of the contrast volume image group. Hereinafter, a score based on the movement amount is called an movement amount score, a score based on the total CT value is called a total CT value score, and a score based on the volume is called a volume score.

When scores for each feature quantity are calculated, the image selection unit 19 selects a combination (hereinafter, called the optimum combination) having the highest degree of similarity of image features of the calcification/stent region from among all combinations of each non-contrast volume image of the non-contrast volume image group and each contrast volume image of the contrast volume image group based on the movement amount score, the average CT value score, the total CT value score, and the volume score.

Figure 7:
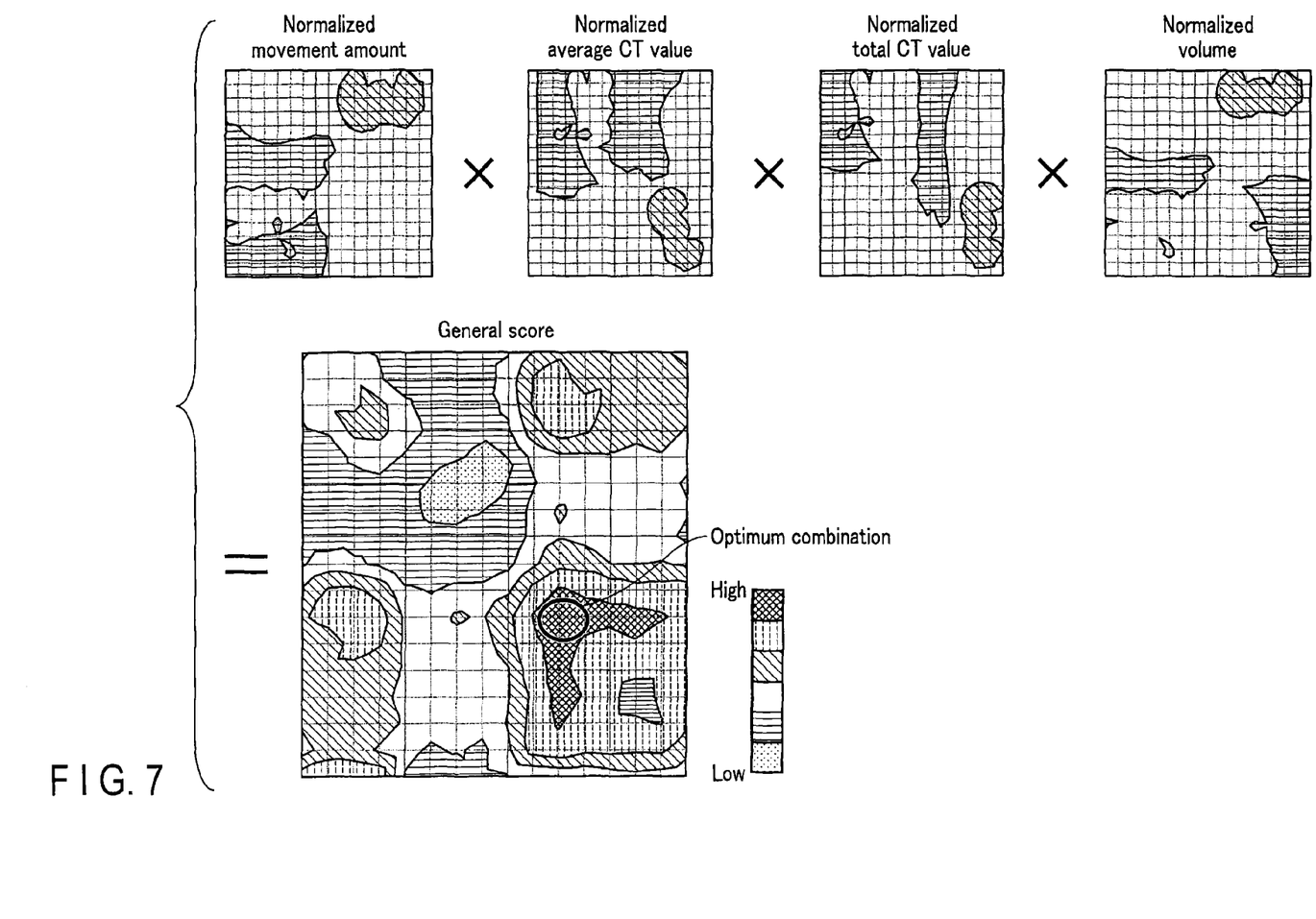
FIG. 7 is a diagram schematically showing selection processing of the optimum combination performed by the image selection unit in step SA4 of FIG. 3A and FIG. 3B.

FIG. 7 is a diagram schematically showing selection processing of the optimum combination by the image selection unit 19. Like in FIG. 6, each hatching pattern in FIG. 7 corresponds to a numerical range of scores. As shown in FIG. 7, the image selection unit 19 first calculates for each combination a score (hereinafter, called a general score) showing the degree of similarity of image features of the calcification/stent region based on the movement amount score, the average CT value score, the total CT value score, and the volume score. As the general score, for example, the product of the movement amount score, the average CT value score, the total CT value score, and the volume score can be cited. With an increasing general score, the calcification/stent region in the non-contrast volume image and the calcification/stent region in the contrast volume image concerning the relevant heart phase have more matching image features dynamically and statically. That is, the calcification/stent region contained in the non-contrast volume image and the calcification/stent region contained in the contrast volume image related to the combination of the highest general score is estimated, among all combinations, to have the least motion of the calcification/stent regions and also ways of movement are most equal. However, the general score is not limited to the product only and may be the sum.

The score based on each feature quantity has a mutually different measure in accordance with the type of the feature quantity. Thus, when compared with a feature quantity of a small measure, a feature quantity of a large measure makes more contributions to the general score. For example, the volume score generally has, when compared with the movement amount score, a large absolute value and makes a major contribution to the general score. To limit such variations of measure, the image selection unit 19 may normalize the score based on each feature quantity to a common scale. For example, the image selection unit 19 normalizes the movement amount score, the average CT value score, the total CT value score, and the volume score to a percentage. The image selection unit 19 calculates a general score based on the normalized movement amount score, the normalized average CT value score, the normalized total CT value score, and the normalized volume score. For example, like the above example, the product of the normalized movement amount score, the normalized average CT value score, the normalized total CT value score, and the normalized volume score may be calculated as a general score.

In addition, the image selection unit 19 may assign weights to scores based on each feature quantity in accordance with properties of each feature quantity.

Figure 8:
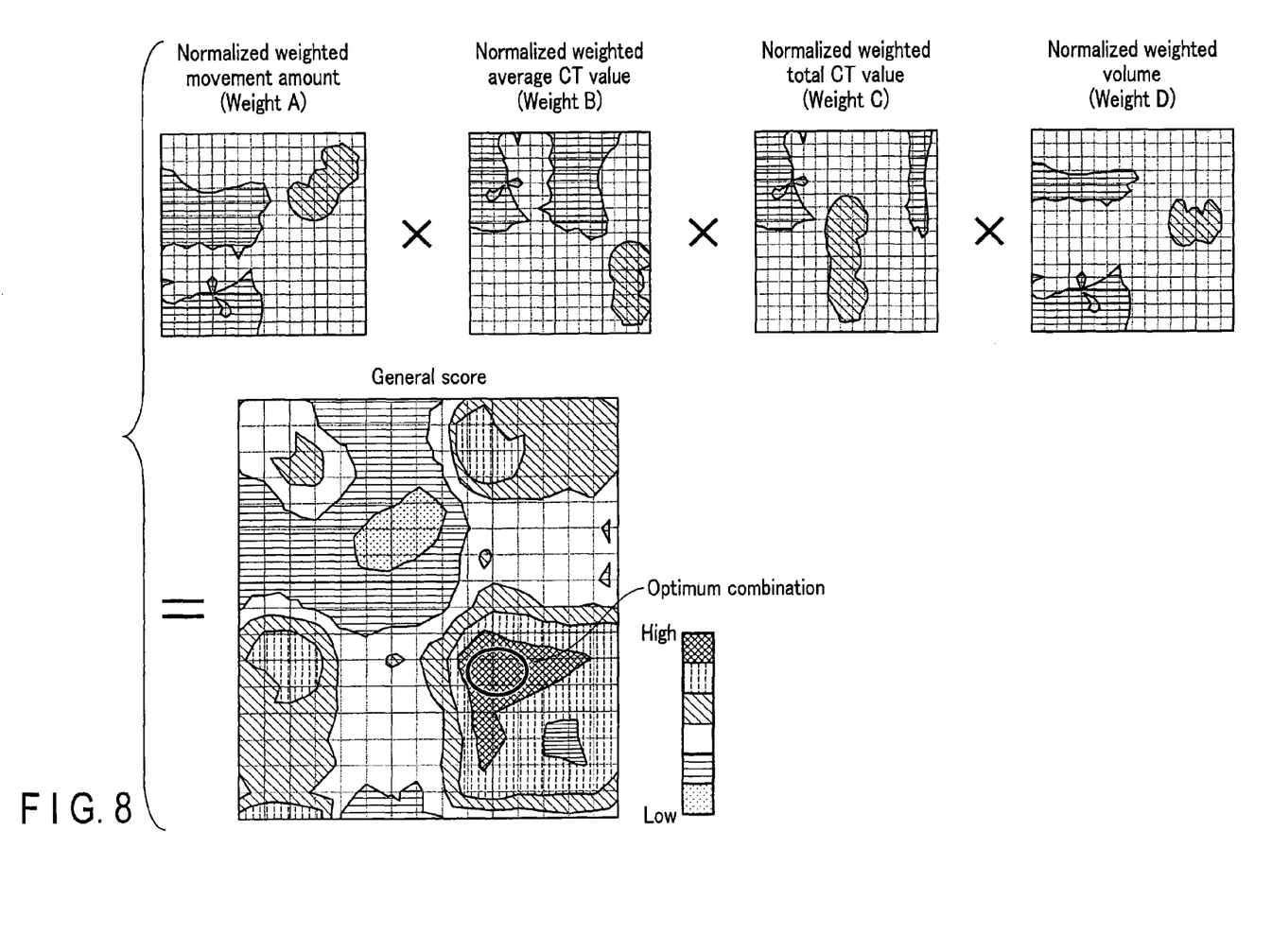
FIG. 8 is a diagram schematically showing selection processing of the combination based on weighted feature quantities performed by the image selection unit in step SA4 of FIG. 3A and FIG. 3B.

FIG. 8 is a diagram schematically showing selection processing of the combination based on weighted feature quantities. Like in FIGS. 6 and 7, each hatching pattern in FIG. 8 corresponds to a numerical range of scores. As shown in FIG. 8, the image selection unit 19 assigns weights in accordance with properties of each feature quantity to scores based on the feature quantities. For example, as shown in FIG. 8, a weight A is assigned to the movement amount score, a weight B is assigned to the average CT value score, a weight C is assigned to the total CT value score, and a weight D is assigned to the volume score. If, for example, the movement amount is considered to make more contributions to dynamics and statics of image features of a calcification/stent region than the average CT value, the total CT value, and the volume, the weight A is set higher than other weights. The weight value can be set to any value by the user via the input device 25.

When weights are assigned, the image selection unit 19 calculates a general score based on the normalized weighted movement amount score, the normalized weighted average CT value score, the normalized weighted total CT value score, and the normalized weighted volume score. For example, like the above example, the product of the normalized weighted movement amount score, the normalized weighted average CT value score, the normalized weighted total CT value score, and the normalized weighted volume score may be calculated as a general score. When weights are assigned, the image selection unit 19 does not necessarily need to normalize scores based on feature quantities.

Thus, the image selection unit 19 identifies the combination of the highest general score from among all combinations of a plurality of non-contrast volume images contained in a non-contrast volume image group and a plurality of contrast volume images contained in a contrast volume image group and automatically selects the non-contrast volume image and the contrast volume image related to the identified combination.

The display 23 displays the selected non-contrast volume image and contrast volume image. More specifically, the display 23 displays the selected non-contrast volume image and contrast volume image side by side or by superimposing one image on the other.

When step SA4 is performed, the control unit 11 causes the subtraction unit 21 to perform subtraction processing (step SA5). In step SA5, the subtraction unit 21 generates a subtraction image based on the non-contrast CT volume image and the contrast CT volume image selected in step SA4.

Figure 9:
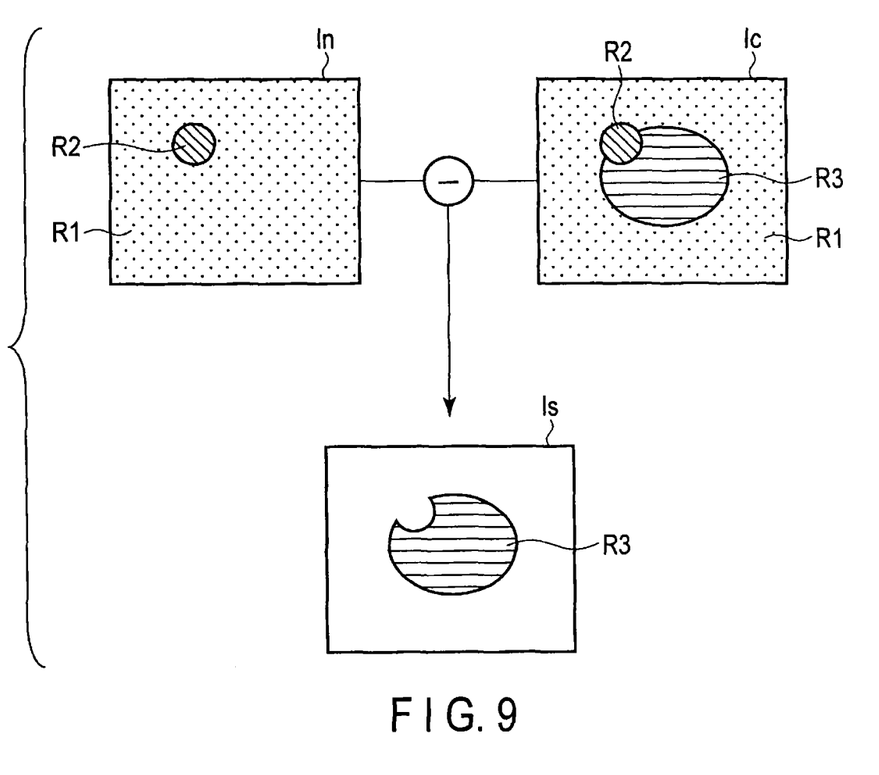
FIG. 9 is a diagram schematically showing generation processing of a subtraction image performed by a subtraction unit in step SA5 of FIG. 3A and FIG. 3B.

FIG. 9 is a diagram schematically showing generation processing of a subtraction image Is by the subtraction unit 21. As shown in FIG. 9, a non-contrast volume image In contains the human body tissue region R1 and the calcification/stent region R2. A contrast volume image Ic contains the human body tissue region R1, the calcification/stent region R2, and the contrast agent region R3. The subtraction unit 21 generates a subtraction image Is by subtracting the non-contrast CT volume image In from the contrast CT volume image Ic. The non-contrast volume image In and the contrast volume image Ic have been selected by the image selection unit 19 in step SA3 and image features of the calcification/stent region R2 in both images substantially match. Therefore, the calcification/stent region R2 contained in the non-contrast volume image In and the calcification/stent region R2 contained in the contrast volume image Ic occupy substantially the same coordinates in volume images and have substantially the same CT value distributions. Thus, the subtraction image Is does not contain the calcification/stent region R2 and contains only the contrast agent region R3, that is, an image region concerning the blood vessel lumen. Therefore, the subtraction image generated in step SA5 has less image artifacts resulting from shifts of image features of the calcification/stent region than a conventional subtraction image based on a non-contrast CT volume image and a contrast CT volume image selected based on the heart phase. The subtraction image is displayed by, for example, the display 23. The subtraction image is also registered with an image server such as PACS via the communication interface 27.

This completes the description of a set of processing related to the selection of the optimum combination of time phases and subtraction processing.

In the above description, the movement amount, the average CT value, the total CT value, and the volume are calculated as feature quantities. However, the present embodiment is not limited to such an example. For example, some of the movement amount, the average CT value, the total CT value, and the volume may not be calculated as feature quantities. By limiting the type of feature quantities, the processing time of a set of processing related to the present application can be reduced.

Objects to be processed in the present embodiment are contrast volume images and non-contrast volume images, but combinations of any images may be selected as objects to be processed. For example, a medical image processing apparatus may select perfusion images and non-contrast volume images as objects to be processed. In this case, there is no need to perform subtraction processing by the subtraction unit 21 on the perfusion image and non-contrast volume image selected by the image selection unit 19 and these images are displayed by the display 23 side by side or by superimposing one image on the other. A perfusion image is an image generated based on a contrast volume image and showing a spatial distribution of blood flow analysis values such as cerebral blood volume (CBV), cerebral blood flow (CBF), and mean transit time (MTT). A first image group and a second image group are not limited to images generated by an X-ray computed tomography apparatus and may be images generated another medical modality than the X-ray computed tomography apparatus such as a magnetic resonance imaging apparatus. In addition, the first image group and the second image group do not necessarily need to be generated by the same medical modality and may be generated by different medical modalities. For example, the first image group may be a CT image group generated by an X-ray computed tomography apparatus and the second image group may be an MR image group generated by a magnetic resonance imaging apparatus. Also, the first image group may be a CT image group generated by an X-ray computed tomography apparatus and the second image group may be a PET image group generated by a PET apparatus.

A medical image processing apparatus according to the present embodiment includes the region extraction unit 15, the parameter calculation unit 17, and the image selection unit 19. The storage 13 extracts an X-ray high-absorbance region concerning an X-ray high-absorbance material from data of a non-contrast volume image of at least one time phase contained in a non-contrast volume image group and data of contrast volume images of a plurality of time phases contained in a contrast volume image group. The parameter calculation unit 17 calculates feature quantities that fluctuate in accordance with motion of an X-ray high-absorbance region for each non-contrast volume image of at least one time phase and each contrast volume image of a plurality of time phases. The image selection unit 19 selects a first non-contrast volume image and a contrast volume image having similar image features in an X-ray high-absorbance region from a non-contrast volume image of at least one time phase and contrast volume images of a plurality of time phases based on calculated feature quantities.

With the above configuration, a medical image processing apparatus according to the present embodiment can automatically select a non-contrast volume image and a contrast volume image having the most similar image features of the X-ray high-absorbance region from each non-contrast volume image contained in a non-contrast volume image group and each contrast volume image contained in a contrast volume image group. Therefore, the medical image processing apparatus according to the present embodiment can automatically select a combination at high speed compared with a conventional example in which the combination of a non-contrast volume image and a contrast volume image is visually selected. Also, the combination can automatically be selected and therefore, any user can output the same combination and subtraction results (that is, a subtraction image) without depending on the user's experience. In addition, the medical image processing apparatus according to the present embodiment outputs a subtraction image based on a non-contrast volume image and a contrast volume image having the most similar image features of the X-ray high-absorbance region and therefore, the occurrence of artifacts resulting from differences of image features of the X-ray high-absorbance region can be reduced to a minimum. As a result, the medical image processing apparatus according to the present embodiment can easily generate a high-quality subtraction image in a short time when compared with the past.

According to the present embodiment, therefore, when two medical images having similar image features are selected from two medical image groups, the optimum combination of the two medical images can easily be selected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus comprising:
   processing circuitry configured to:
   extract an image region having an image element value larger than a predetermined image element value from a first image of a plurality of time phases collected in first non-contrast CT imaging and second images of a plurality of time phases collected in second contrast CT imaging;
   calculate a feature quantity that fluctuates in accordance with motion of the image region for the first image of the plurality of time phases and the second images of the time phases, calculate a plurality of feature quantity scores corresponding to respective types of the feature quantity for the first image of at least the one time phase and the second images of the time phases, and calculate general scores based on the feature quantity scores for all combinations of the first image of at least the one time phase and the second images of the time phases;
   select the first image and the second image related to the combination with the highest general score from among all the combinations of the first image and the second images; and
   generate a subtraction image based on the selected first image and the selected second image.

2. The medical image processing apparatus according to claim 1, wherein the first image of at least the one time phase and the second images of the time phases are associated with a heart phase or a breathing phase.

3. The medical image processing apparatus according to claim 1, wherein the processing circuitry is configured to:
   generate a first mask image in which other image regions than the image region is set as a mask region based on the first image of a predetermined time phase of the first image of at least the one time phase,
   generate a second mask image in which the other image regions than the image region is set as the mask region based on the second image of a predetermined time phase of the second images of the time phases, extract the image region from each of the first images of at least the one time phase by performing mask processing on the first image of at least the one time phase using the first mask image, and extract the extracted image region from each of the second images of the time phases by performing the mask processing on the second images of the time phases using the second mask image.

4. The medical image processing apparatus according to claim 3, wherein the processing circuitry is configured to expand the image region by a predetermined number of image elements and sets the other image regions than the expanded image region as the mask region.

5. The medical image processing apparatus according to claim 1, wherein the processing circuitry is configured to calculate, as the feature quantity, a plurality of types of the feature quantity based on an image element value and a number of image elements of the image region.

6. The medical image processing apparatus according to claim 5, wherein the processing circuitry is configured to calculate at least one of a movement amount, an average image element value, a total image element value, and a volume of the image region in a target time phase with respect to a time phase prior to or subsequent to the target time phase as the types of the feature quantity.

7. The medical image processing apparatus according to claim 6, wherein the processing circuitry is configured to calculate a plurality of feature quantity scores corresponding to the respective types of the feature quantity for the first image of at least the one time phase and the second images of the time phases, calculate general scores based on the feature quantity scores for all combinations of the first image of at least the one time phase and the second images of the time phases, and select the first image and the second image related to the combination with the highest general score from among all the combinations.

8. The medical image processing apparatus according to claim 7, wherein the processing circuitry is configured to calculate a product of the types of the feature quantity as the feature quantity score and the product of the feature quantity scores as the general score.

9. The medical image processing apparatus according to claim 7, wherein the processing circuitry is configured to normalize the types of feature quantity scores to a common scale and calculates the general score based on the normalized feature quantity scores.

10. The medical image processing apparatus according to claim 7, wherein the processing circuitry is configured to assign weights to the types of feature quantity scores and calculates the general score based on the weighted feature quantity scores.

11. The medical image processing apparatus according to claim 1, wherein the processing circuitry is configured to extract the image region concerning at least one of a calcification portion and a stent as the image region.

* * * * *